United States Patent
Sieben et al.

[11] Patent Number: 5,820,548
[45] Date of Patent: Oct. 13, 1998

[54] APPARATUS FOR TREATING MALIGNANT TISSUE CHANGES

[75] Inventors: Ulrich Sieben, Reute; Michael Kraus, Titisee-Neustadt; Bernhard Wolf, Stegen, all of Germany

[73] Assignee: Micronas Intermetall GmbH, Freiburg, Germany

[21] Appl. No.: 784,845

[22] Filed: Jan. 15, 1997

[30] Foreign Application Priority Data

Jan. 17, 1996 [DE] Germany ............... 196 01 487.5

[51] Int. Cl.⁶ ................................ A61M 5/00
[52] U.S. Cl. ........................... 600/361; 604/66
[58] Field of Search ............... 604/50, 65–67, 604/20; 600/361, 562; 128/897, 898; 606/32, 33, 34, 41, 42; 607/2, 3, 62, 901

[56] References Cited

U.S. PATENT DOCUMENTS

| | | |
|---|---|---|
| 4,003,379 | 1/1977 | Ellinwood, Jr. . |
| 4,402,694 | 9/1983 | Ash et al. . |
| 4,784,158 | 11/1988 | Okimoto . |
| 4,800,899 | 1/1989 | Elliott . |
| 5,135,479 | 8/1992 | Sibalis et al. . |
| 5,301,688 | 4/1994 | Stephen et al. . |
| 5,396,897 | 3/1995 | Jain et al. ............... 600/562 |
| 5,413,915 | 5/1995 | Case et al. . |

FOREIGN PATENT DOCUMENTS

| | | |
|---|---|---|
| 0 236 285 A2 | 9/1987 | European Pat. Off. . |
| 33 21 831 A1 | 11/1983 | Germany . |
| 36 01 730 C2 | 9/1991 | Germany . |
| 42 41 128 A1 | 6/1993 | Germany . |
| 43 00 018 A1 | 3/1995 | Germany . |
| WO94/05361 | 3/1994 | WIPO . |
| WO94/08655 | 4/1994 | WIPO . |

OTHER PUBLICATIONS

Akhurst et al., "A Perfusion Loss Computer For Use In Cancer Treatment," *Instruments And Control Systems*, vol. 36, pp. 148–151, 1963.

James B. Brinton, "System To Detect And Treat Cancer, Using Microwaves For Both Tasks," *Electronics International*, vol. 26, p. 42, 1979.

*Primary Examiner*—Lee S. Cohen
*Assistant Examiner*—Eric F. Winakur
*Attorney, Agent, or Firm*—Panitch Schwarze Jacobs & Nadel, P.C.

[57] ABSTRACT

An apparatus 1 serves for treating tumors in particular. This apparatus has, for example, a sensor-actuator head 3 with at least one sensor 10 for determining the acidification of the immediate surroundings of the tumor cells. An active ingredient dispensing device for exerting chemical influence and/or electrodes for exerting physical influence through electrical and/or electromagnetic fields on the tumorous tissue area to be treated are provided on the sensor-actuator head. The sensor(s) 10 as well as the active ingredient dispensing facility and/or the treatment electrodes are connected with a control facility for controlling chemical and/or physical treatment of the tumorous tissue area as a function of measured values.

20 Claims, 2 Drawing Sheets

Fig. 1
Fig. 3
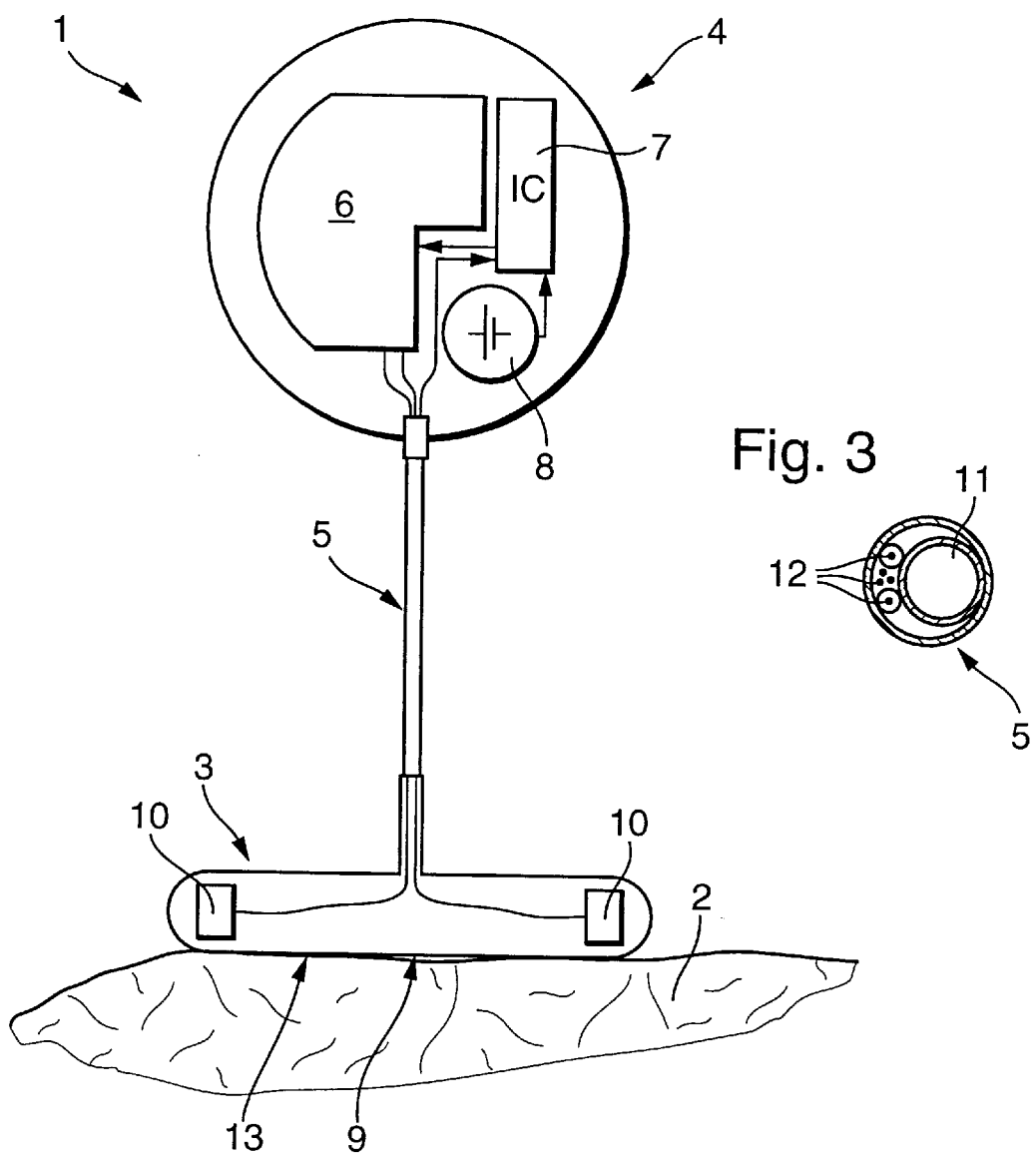
Fig. 2
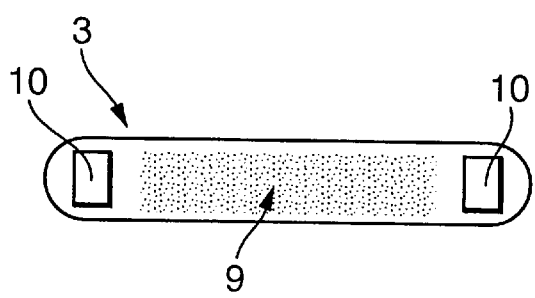

APPARATUS FOR TREATING MALIGNANT TISSUE CHANGES

BACKGROUND OF THE INVENTION

The invention concerns an apparatus for treating malignant tissue changes. It is already known in cancer therapy to use chemotherapeutic agents which are supposed to injure pathogenic organ parts, but as far as possible not the rest of the organism.

The systemic and localized dosing of chemotherapeutic agents is, however, problematic since, on the one hand, a high efficiency against a tumor, for example, is sought through an appropriate active ingredient concentration. On the other, however, the danger of damaging healthy tissue then exists through unspecified absorption.

BRIEF SUMMARY OF THE INVENTION

An object of the present invention is to create an apparatus with which a target-oriented chemotherapy is possible, in which stress and injury to unrelated areas of the body are at least largely reduced. For accomplishing this object, it is proposed that the apparatus have a sensor-actuator head with at least one sensor for determination of acidification of the immediate surroundings of the tumor cells, that an active ingredient administration device for exerting chemical influence and/or electrodes for exerting physical influence through electric and/or electromagnetic fields on the tumorous tissue area to be treated be provided in the sensor-actuator head, and that the sensor(s) as well as the active ingredient administration device and/or treatment electrodes be connected with a control facility for controlling a chemical and/or physical treatment of the tumorous tissue area as a function of the measured acidity values.

With this apparatus, a medical ingredient can be directly applied for exerting chemical influence to a tumor to be treated, and at the same time a continuous monitoring also takes place there in the immediate vicinity of the treatment site with the aid of sensor(s) during treatment. On the basis of the values measured by the sensor(s), the dosage can be adapted by the control facility to predetermined ideal values. Consequently, an independently operating feedback loop is formed through which a continuous dosage tracking can be undertaken with the active ingredient to be applied.

For monitoring the treatment area, at least one sensor is provided for determining the acidity in the treatment area, since changes in the pH value permit inferences about the metabolic activities of the tumor cells. Appropriate treatment adaptations can thereby be undertaken. Underlying this is the knowledge that the growth and spread of tumors must be regarded as a process of cellular self-organization which, apart from changes in the cellular signal processing apparatus, are basically controlled by the microenvironment of the tumor. In this connection, the pH value of the microenvironment of the tumor plays a central, key role.

If, for example, an ideal pH value of 7.4 is preset, the control facility undertakes a regulated dosage of the medical active ingredient on the basis of measuring the pH present as an observed value until the ideal value, in the example pH 7.4, is reached. The medical active ingredient can be an active substance for neutralizing the pH gradient. Furthermore, an active substance (antagonist) for blocking the proton pump on the cell membranes of the tumor cells or an active substance for blocking the molecular biological agents (for example antisense products) can be considered. Instead of or in combination with the chemical action on the tumor tissue, physical action can also be undertaken. This can occur through electrical and/or electromagnetic fields via electrodes on the sensor-actuator bead by means of iontophoresis. Direct current or alternating-current voltage can be applied to the electrodes. Changing the field as a function of the respective measured value is also undertaken here, so that even in this regard, a control loop and consequently a targeted treatment with "feedback" is available.

A pH sensor based on a semiconductor or a pH sensor based on a conductivity and impedance measurement can be provided as a sensor for determining the acidity of the immediate surroundings of the tumor cells. A high degree of measurement accuracy can be attained with a pH sensor based on semiconductors. A sensor based upon conductivity and impedance measurement can be more easily used in certain applications (e.g., liver, stomach).

If need be, another sensor, especially an ion or molecular sensor, is provided in addition to the at least one pH sensor. Additional, therapy-relevant changes besides pH value in the microenvironment of a tumor can be registered with these additional sensors. Appropriate measures for applying the medical active ingredient can be derived from these additional measurement data.

Appropriately, the active ingredient dispensing device preferably has at least one porous membrane and an active ingredient supply to this membrane, whereby a dosing facility, which is connected to a dosage control, is situated in association with the ingredient supply. A locally-restricted and dosed feed of the active ingredient is thereby possible.

The sensor(s), as well as the optionally-provided porous membrane, thereby form a support and contact surface for the tissue area to be treated. At least two electrodes for iontophoretic purposes, which are connected with a voltage source by electrical lines, can also be provided in association with this support and contact surface for the tissue area to be treated.

One embodiment of the invention provides that the sensor-actuator head forms a complete functional unit. For exerting a chemical influence, this can have at least one active ingredient storage container, one or more dosing facilities with dosing control connected with the porous membrane or the like, as well as at least one pH sensor. On the other hand, for exerting a physical influence, there also exists the possibility that the functional unit has at least one pH sensor, at least two electrodes for iontophoretic purposes, a voltage source, as well as a control facility. When needed, the functional unit can have facilities for a chemical as well as for a physical treatment or action. Such a device can be used as a complete unit suitable for function within the body, and remain there over a designated treatment period. Since all components necessary for function are present, an external connection is not necessary with this embodiment.

According to another embodiment of the invention, however, there also exists the possibility of the active ingredient storage container, preferably together with the dosing facility and dosage control, being arranged remote from the sensor-actuator head, and one or more lead wires being provided between these functional groups, especially for dosed feeding of the active ingredient to the sensor-actuator head and/or for connection with the electrodes. The sensor-actuator head itself can be constructed especially small with this embodiment, so that it can also be used in difficult to access places within the body. Moreover, there exists in this connection the possibility that the supply unit, which is remote from the sensor-actuator head, is arranged to be easily accessible so that refilling the medical active ingredient, possible external current provision and the like can be easily realized.

Attachment regions, preferably for adhesive attachment of the sensoractuator head to the tissue area to be treated, are preferably provided in connection with the support and contact surface of the sensor-actuator head, particularly on the side edges In this way, the sensor-actuator head can be fastened on the area to be treated simply by setting and pressing it on, and additional attachment measures are thereby unnecessary. It is advantageous in this regard if the attachment regions of the sensor-actuator head are constructed so as to conduct electricity and at the same time serve as electrodes for iontophoresis. This saves space and simplifies the construction of the sensor-actuator head.

BRIEF DESCRIPTION OF THE SEVERAL VIEWS OF THE DRAWING

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

FIG. 1 is a somewhat schematic representation of an apparatus of the invention with a sensor-actuator head as well as a supply unit arranged remote from it and connected through a lead wire;

FIG. 2 is an underside view of the sensor-actuator head depicted in FIG. 1;

FIG. 3 is a sectional representation of the lead wire between the sensor-actuator head and supply unit in accordance with FIG. 1;

DETAILED DESCRIPTION OF THE INVENTION

Figure 4:
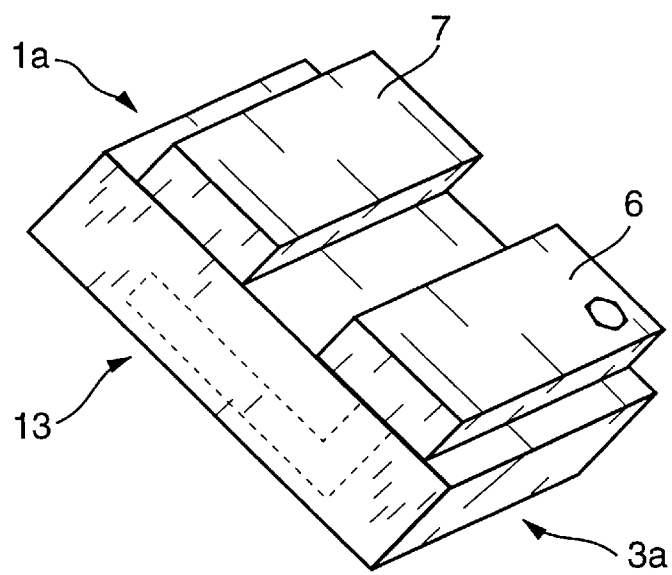
FIG. 4 is another embodiment of the apparatus of the invention in perspective representation.

An apparatus 1 depicted in FIG. 1 serves to apply medical active ingredients in a region of living cell tissue. In this connection, it can in particular be a matter of a tumor 2 to be treated which is indicated in FIG. 1.

The apparatus 1 has a sensor-actuator head 3, a supply unit 4 remote from this sensor-actuator head 3 in the embodiment in accordance with FIG. 1, as well as a lead wire 5 between the sensor-actuator head 3 and the supply unit 4. An active ingredient storage container 6, preferably with a dosing facility (not depicted in detail here) as well as a dosing control 7 and a current supply 8, are located within the supply unit 4.

The sensor-actuator head 3 has on its support and contact surface 13 a porous membrane 9 (see also FIG. 2), an active ingredient supply to this membrane 9, as well as sensors 10 adjacent to the membrane. The membrane 9 as well as the sensors 10 make contact with the treatment area in the application position. Within the lead wire 5, which can be constructed as a catheter tube in a practical embodiment, the medical active ingredient can be fed from the storage container 6 to the porous membrane 9. Furthermore, electrical connections between the sensor(s) 10 and the dosing control 7 are also accommodated in the lead wire 5. This is easily seen in the cross sectional representation in accordance with FIG. 3. The connecting tube for the active ingredient is here designated with 11 and the electrical lines with 12.

With the aid of the apparatus of the invention, medical active ingredients can be applied directly to the area to be treated, for example a tumor 2. For this, the sensor-actuator head 3 is placed directly on the area to be treated, and the medical active ingredient can then be fed to this area via the porous membrane 9. Monitoring the treatment area can take place with the aid of the sensors 10, and on the basis of measured results an exact adaptation of the ingredient dosing can take place by means of the dosing control 7 connected with the sensors 10.

In this regard, at least one of the sensors 10 is a pH sensor, since monitoring the pH value of the microenvironment of the area to be treated and influencing this environment by variation of the pH value, especially through appropriate administration of active ingredient, is of essential significance for a successful immune therapy. Other chemotherapeutic concepts also depend upon the steep, extracellular pH gradients being reduced.

Several pH sensors can also be provided within the application area, whereby two or more pH sensors can be arranged at a distance to one another for an extracellular gradient measurement. Preferably, ion selective field effect transistors (IS-FET) are used as pH sensors.

Moreover, still further sensors 10, especially ion or molecular sensors, can be provided in order to obtain still more strongly indicative measurement results of the microenvironment of the area to be treated. A very directed, effective treatment is then possible therewith.

Figure 5:
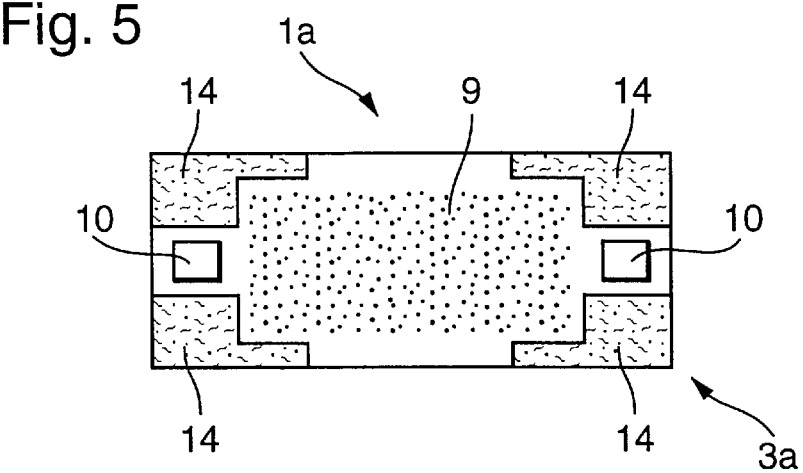
FIG. 5 is an underside view of the apparatus illustrated in FIG. 4.

FIGS. 4 and 5 depict a modified embodiment of an apparatus 1a, in which the sensor-actuator head 3a forms a complete functional unit. This sensoractuator head 3a also contains all structural components which are accommodated in the supply unit 4 in the embodiment according to FIG. 1. A compact unit, which can remain inside the body over an appropriate treatment period as an autonomous unit, emerges with this embodiment of the apparatus 1a.

The underside view in accordance with FIG. 5 depicts, also in the area of the support and control surface 13, within which the porous membrane 9 as well as the sensor(s) 10 is/are located, attachment regions 14 arranged in the corner regions and/or on the side edges. By means of these attachment regions 14, the sensor-actuator head 3a, and/or also the sensor-actuator head 3 in accordance with FIGS. 1 and 2, can be pressed on the area to be treated and then be held by adhesive attachment.

The attachment regions 14 can also be used for iontophoretic purposes, and are then constructed so as to conduct electricity and to be connected with a voltage source via connecting leads. An exchangeable and rechargeable battery 8 (FIG. 1) can be provided as current supply for dosage control, or there exists instead the possibility of providing a thermoelectric or a galvanic current supply with the aid of body fluids. Thermoelectric or galvanic current supplies are especially advantageous in connection with the embodiment of the apparatus of the invention depicted in FIGS. 4 and 5.

Figure 6:
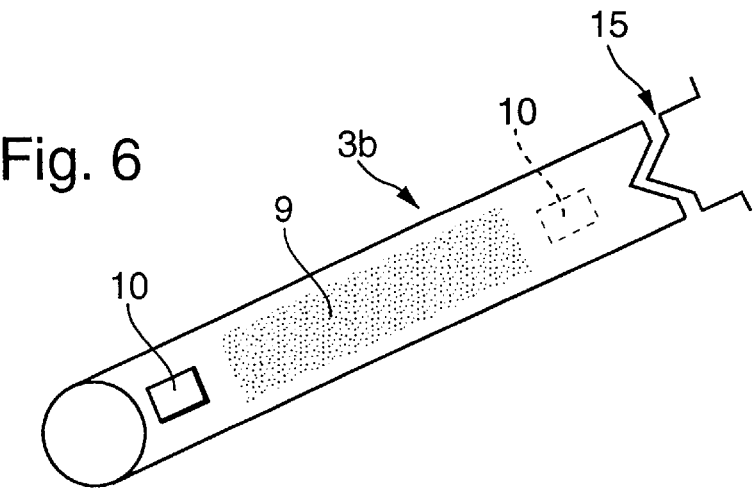
FIG. 6 is a tube-shaped construction of a sensor-actuator head for use in hollow organs with a view on the contact surface.

FIG. 6 shows a still further construction variant of a sensor-actuator head 3b, which is basically constructed in the form of a tube and has a strip-like longitudinally oriented support and contact surface 13 on its outer jacket surface. This embodiment finds application especially for treatment within hollow organs. It should be mentioned in this connection that several support and contact surfaces 13 can also be provided distributed on the periphery of the tube-like sensor-actuator head. The other embodiments of application heads can also be equipped with several support and contact surfaces and with porous membranes 9 and sensors 10 situated within these. A connection 15 for an external active ingredient container, especially for refilling with active ingredient, is indicated on the end of the tube-like sensor-actuator head 3b.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. An apparatus for treating malignant tissue changes, comprising a sensor-actuator head having at least one sensor for measuring acidity values of an environment adjacent to malignant tissue cells, at least one of a dispensing device for providing an active ingredient for chemical action and treatment electrodes for effecting a physical action through electric and/or electromagnetic fields being provided on the sensor-actuator head for application to an area of malignant tissue to be treated, wherein the at least one sensor and the ingredient dispensing device and/or the treatment electrodes are connected with a control facility for controlling a chemical and/or physical treatment of the malignant tissue area, the control facility being guided as a function of the acidity values measured by the at least one sensor.

2. The apparatus according to claim 1, wherein the active ingredient dispensing device comprises at least one porous membrane and an active ingredient supply for the membrane, and wherein the control facility comprises a dosing control which is connected with the active ingredient supply.

3. The apparatus according to claim 2, wherein the at least one sensor is arranged adjacent to the at least one membrane and the sensor and membrane together form a surface for supporting and contacting the malignant tissue area to be treated.

4. The apparatus according to claim 1, wherein the at least one sensor forms a surface for supporting and contacting the malignant tissue area to be treated.

5. The apparatus according to claim 4, wherein at least two said electrodes connected with a voltage source via electric lines are provided on the supporting and contacting surface.

6. The apparatus according to claim 4, wherein at least side edges of the supporting and contacting surface are provided with attachment regions for adhesive attachment of the sensor-actuator head to the malignant tissue area to be treated.

7. The apparatus according to claim 6, wherein the attachment regions are constructed so as to conduct electricity and serve as said electrodes.

8. The apparatus according to claim 4, comprising a plurality of spaced-apart sensors arranged on the supporting and contacting surface.

9. The apparatus according to claim 1, wherein the sensor for measuring acidity values is one of a pH sensor based on a semiconductor and a pH sensor based on conductivity and impedance measurement.

10. The apparatus according to claim 9, wherein at least one ion selective field effect transistor (IS-FET) is provided as a pH sensor.

11. The apparatus according to claim 1, wherein said sensor-actuator head has an ion or molecular sensor and at least one pH sensor.

12. The apparatus according to claim 1, wherein the sensor-actuator head forms a functional unit.

13. The apparatus according to claim 12, wherein the functional unit includes at least one active ingredient storage container, a dosing control connected with at least one porous membrane, and at least one pH sensor.

14. The apparatus according to claim 12, wherein the functional unit includes at least one pH sensor, at least two electrodes for iontophoretic purposes, a voltage source, and the control facility.

15. The apparatus according to claim 1, wherein the sensor-actuator head has an essentially tube-shaped construction.

16. The apparatus according to claim 15, wherein the essentially tube-shaped sensor-actuator head has on its outer surface at least one strip-shaped surface for supporting and contacting the malignant tissue area to be treated, the strip-shaped surface being oriented along a longitudinal axis of the tube-shaped sensor-actuator head.

17. The apparatus according to claim 15, further comprising a connection provided on the sensor-actuator head for an external ingredient container for refilling the active ingredient.

18. The apparatus according to claim 1, comprising an active ingredient storage container and a dosing control arranged remote from the sensor-actuator head, and at least one lead conduit from the container and control for dosed feeding of the active ingredient to the sensor-actuator head.

19. The apparatus according to claim 18, wherein the lead conduit also includes at least one wire for connecting a voltage source with the electrodes.

20. The apparatus according to claim 1, further comprising at least one of a battery, a thermoelectric current supply, and a galvanic current supply adopted to generate the current with aid of body fluids, provided as a current source for the electrodes.

* * * * *